(12) United States Patent (10) Patent No.: US 9,295,538 B2
Koyfman et al. (45) Date of Patent: *Mar. 29, 2016

(54) METHODS OF REPAIRING A HERNIA USING A HERNIA SUPPORT DEVICE

(71) Applicant: Ethicon, Inc., Somerville, NJ (US)

(72) Inventors: Ilya S. Koyfman, Ringoes, NJ (US); Uri Herzberg, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 215 days.

This patent is subject to a terminal disclaimer.

(21) Appl. No.: 13/791,934

(22) Filed: Mar. 9, 2013

(65) Prior Publication Data

US 2013/0190785 A1 Jul. 25, 2013

Related U.S. Application Data

(62) Division of application No. 11/904,200, filed on Sep. 26, 2007, now Pat. No. 8,500,759.

(51) Int. Cl.
*A61F 2/02* (2006.01)
*A61B 17/08* (2006.01)
*A61F 2/00* (2006.01)

(52) U.S. Cl.
CPC ............ *A61F 2/0063* (2013.01); *A61F 2/0095* (2013.01)

(58) Field of Classification Search
CPC ........... A61F 2/0063; A61F 2002/0068; A61F 2220/0016; A61F 2/0095
See application file for complete search history.

(56) References Cited

U.S. PATENT DOCUMENTS

| | | |
|---|---|---|
| 3,416,524 A | 12/1968 | Meier |
| 4,865,026 A | 9/1989 | Barrett |
| 5,007,916 A | 4/1991 | Linsky et al. |
| 5,147,374 A | 9/1992 | Fernandez |
| 5,356,432 A | 10/1994 | Rutkow et al. |
| 5,397,331 A * | 3/1995 | Himpens et al. .............. 606/151 |
| 5,425,740 A | 6/1995 | Hutchinson, Jr. |
| 5,634,931 A | 6/1997 | Kugel |

(Continued)

FOREIGN PATENT DOCUMENTS

| | | |
|---|---|---|
| EP | 0130037 | 1/1985 |
| EP | 0898944 | 3/1999 |

(Continued)

OTHER PUBLICATIONS

Written Opinion of the International Searching Authority in PCT/US208/076496 mailed Mar. 30, 2010.

*Primary Examiner* — Christopher L Templeton
(74) *Attorney, Agent, or Firm* — Doherty IP Law Group LLC

(57) ABSTRACT

A method of repairing a hernia using a hernia mesh support device includes providing a hernia mesh support device, reducing a hernia within a patient's abdomen, inserting the hernia mesh support device into the abdomen and positioning the device in alignment with the hernia, ensuring that no abdominal organs are present between the device and the abdominal wall, whereby the step of ensuring that no abdominal organ is between the device and the abdominal wall includes the step of digitally sweeping the space between the abdominal wall and the device, removing a protective cover, and pulling on a pull strap joined to an inner ring to place the device tightly against the abdominal wall and to anchor barbed pins and hollow needles into the abdominal wall.

20 Claims, 2 Drawing Sheets

(56) References Cited

U.S. PATENT DOCUMENTS

| | | |
|---|---|---|
| 5,695,525 A | 12/1997 | Mulhauser et al. |
| 5,836,961 A | 11/1998 | Kieturakis et al. |
| 5,972,008 A | 10/1999 | Kalinski et al. |
| 6,152,144 A | 11/2000 | Lesh et al. |
| 6,171,318 B1 | 1/2001 | Kugel et al. |
| 6,174,320 B1 | 1/2001 | Kugel et al. |
| 6,224,616 B1 | 5/2001 | Kugel |
| 6,267,772 B1 | 7/2001 | Mulhauser et al. |
| 6,383,201 B1 | 5/2002 | Dong |
| 6,436,030 B2 | 8/2002 | Rehil |
| 6,447,524 B1 | 9/2002 | Knodel et al. |
| 6,599,318 B1 | 7/2003 | Gabbay |
| 6,623,492 B1 | 9/2003 | Berube et al. |
| 6,652,555 B1 | 11/2003 | VanTassel et al. |
| 6,669,735 B1 | 12/2003 | Pelissier |
| 6,712,822 B2 | 3/2004 | Re et al. |
| 6,736,823 B2 | 5/2004 | Darois et al. |
| 6,790,213 B2 | 9/2004 | Cherok et al. |
| 6,808,487 B2 | 10/2004 | Migliari |
| 6,926,723 B1 | 8/2005 | Mulhauser et al. |
| 6,966,916 B2 | 11/2005 | Kumar |
| 2001/0044637 A1 | 11/2001 | Jacobs et al. |
| 2002/0042658 A1 | 4/2002 | Tyagi |
| 2002/0049503 A1 | 4/2002 | Milbocker |
| 2002/0103494 A1 | 8/2002 | Pacey |
| 2003/0004581 A1 | 1/2003 | Rousseau |
| 2003/0130745 A1 | 7/2003 | Cherok et al. |
| 2004/0049207 A1 | 3/2004 | Goldfarb et al. |
| 2004/0087980 A1 | 5/2004 | Ford et al. |
| 2004/0087981 A1 | 5/2004 | Berube et al. |
| 2004/0092969 A1 | 5/2004 | Kumar |
| 2004/0204723 A1 | 10/2004 | Kayan |
| 2005/0010239 A1 | 1/2005 | Chefitz |
| 2005/0049636 A1 | 3/2005 | Leiboff |
| 2005/0113858 A1 | 5/2005 | Duetsch |
| 2005/0256532 A1* | 11/2005 | Nayak et al. ................... 606/151 |
| 2006/0083767 A1 | 4/2006 | Deusch et al. |
| 2006/0189918 A1* | 8/2006 | Barker ............................ 604/13 |
| 2006/0212050 A1 | 9/2006 | D'Agostino et al. |
| 2006/0235543 A1* | 10/2006 | Sogaard-Andersen .... 623/23.64 |
| 2006/0282105 A1 | 12/2006 | Ford et al. |
| 2007/0083229 A1 | 4/2007 | Deutsch |
| 2008/0147200 A1 | 6/2008 | Rousseau et al. |
| 2008/0255593 A1* | 10/2008 | St-Germain ................... 606/151 |

FOREIGN PATENT DOCUMENTS

| | | |
|---|---|---|
| EP | 1199037 | 4/2002 |
| WO | 9529635 | 11/1995 |
| WO | 0189392 | 11/2001 |
| WO | 03034925 | 5/2003 |
| WO | 2004012627 | 2/2004 |
| WO | 2004071349 | 8/2004 |
| WO | 2004103162 | 12/2004 |
| WO | 2005007219 | 1/2005 |

* cited by examiner

METHODS OF REPAIRING A HERNIA USING A HERNIA SUPPORT DEVICE

CROSS REFERENCE TO RELATED APPLICATIONS

The present application claims benefit of commonly assigned U.S. patent application Ser. No. 11/904,200, filed Sep. 26, 2007, now U.S. Pat. No. 8,500,759, the disclosure of which is hereby incorporated by reference herein.

BACKGROUND OF THE INVENTION

1. Field of the Invention

The present application is directed to surgical devices, and more particularly relates to mesh surgical devices for hernia repair.

2. Description of the Related Art

The layer or layers of fascia that lie in the abdominal wall and surround the peritoneal cavity are the strong structures that maintain the integrity of the peritoneal cavity. If there is a defect in the fascia, abdominal contents may penetrate through the weaker layers of the abdominal wall (comprised of muscle or fat) and push ahead or through the thin lining (peritoneum) of the abdominal cavity so that the abdominal contents, such as omentum or bowel and become trapped.

The squeezing of viscera through a facial defect can cause pain. When a visceral structure becomes trapped outside the fascial plane, it is incarcerated. Incarcerated viscera can be strangulated by a narrow facial defect, producing ischemic necrosis. This may lead to toxemia, infection, bacteremia and death if not surgically repaired. It is therefore preferable that hernia be repaired early, prior to becoming incarcerated or strangulated.

In modern practice, hernia repair is often accomplished by implanting a surgical prosthesis, such as a hernia patch (or mesh), over a fascial defect. The patch is fixed to the surrounding tissue with sutures or fasteners. The hernia patch prevents the herniation of the abdominal viscera through a defect in the fascial layer. This technique is preferred over direct suture closure of the fascial defect, as it avoids the exertion of excessive tension on the musculofascial tissue and thereby makes it less likely for the hernia to recur. Hernia repair with prosthetic patches can be accomplished via an open or laparoscopic approach.

The mesh or patch used for hernia repair can be in direct contact with the structures in the abdominal cavity, for example, the intestines, so that there is a tendency for adhesions to form in between these structures. Such adhesions are known to be responsible for certain occasionally serious complications.

Many conventional hernia patches are made of a thin, flexible material. The limited visibility and maneuverability available to the surgeon, and the fact that many hernia patches tend to become folded, stretched or gathered when being positioned, may lead to disorientation and improper placement and/or fixation of a hernia patch. This may result in a failure to cover the entire hernia defect, or improper tension on the patch. Such errors may result in the recurrence of the hernia.

Another problem with conventional hernia repair devices is that, once applied, they can entrap the intestines or omentum between the tissue where the repair device is applied and the device itself.

Some commercially available devices have stiffening elements at the edge of the device coupled with straps placed in the middle of the device. Upon pulling the straps, the outer edge of the device is brought in proximity to the peritoneum. Other approaches have been to repair the hernia via a pre-peritoneal approach, thereby avoiding the issue of entrapment altogether. The problem with the first design has been that it can buckle if the straps are pulled too hard. Also, if the stiffening element was made from a bioabsorbable material, it would degrade and lose its stiffness prematurely, possibly causing the intestines to become entrapped between the device and the peritoneum. The issue with the second approach is that it necessitates the creation of a space to insert the device thereby forming a potential "dead space" where a seroma may form. This approach requires a greater level of skill to implement and has the potential of perforating the peritoneum.

Attaching adhesion barriers to the part of the device that faces the abdominal content is another approach. This prevents adhesion of the intestines to the visceral side of the device, but does not prevent intestinal entrapment between the device and the peritoneum. Indeed, it is preferable that the side of the device that faces the peritoneum (in devices that are implanted intraperitoneally) is made from a material that encourages tissue integration. This, in turn, carries the risk that if the intestines or omentum is entrapped between the device and the peritoneum, the entrapped tissue will integrate firmly with the device.

Some conventional hernia repair devices require the surgeon to anchor the device to the peritoneum or pre-peritoneal tissue layers by sutures that are placed blindly. More specifically, the suture needle in accordance with this procedure is inserted through the muscular layer and the fascia to anchor the hernia repair device, and is then returned through the fascia and muscular layers. This blind technique to anchor the repair device carries the risk of injuring underlying tissues, such as the intestines, liver, spleen and vasculature.

A "suture-passer" device has been employed to facilitate the fixation of the hernia repair device to the peritoneum with sutures. Grasping and feeding of the suture into the grasping arm of the "suture passer" within the abdomen and fixation or suturing-of the mesh to the abdominal wall are technically difficult, cumbersome and time consuming.

U.S. Patent Publication No. 2001/0044637, having Daniel Jacobs and Robert James Elson as named inventors, discloses tension systems with barbs which are stated to be capable of holding tissues together. The problem with using such a tensioning system is that the insertion of barbs into the abdomen carries the risk of injuring the abdominal contents. It is only when the contact with the peritoneum is complete, without any obstructions, that such barbs are of potential benefit. If the barbs come in contact with any abdominal organs, the risk of injuring such organs is significant, as these organs are typically fragile. Moreover, even superficial injury to abdominal contents will increase the risk of adhesions of an organ to another.

SUMMARY OF THE INVENTION

It is an object of the present invention to provide a surgical device for repairing a hernia which has self-anchoring means that securely attaches to the peritoneum or pre-peritoneal layers, while protecting abdominal organs.

It is another object of the present invention to provide an improved method for repairing a hernia.

It is yet another object of the present invention to provide a method and a surgical device for use in hernia repair that avoid the problems associated with the blind suturing approach when attaching the device to the abdominal wall.

It is a further object of the present invention to provide a method and device for hernia repair that is safe and easy to use.

It is yet a further object of the present invention to provide a method of hernia repair that allows better incorporation of a hernia device into the peritoneum, thereby increasing the degree of tissue integration with the device.

It is still another object of the present invention to provide a method and device for hernia repair that minimize the possibility of intestinal entrapment during the repair procedure.

It is yet a further object of the present invention to provide a method and device for hernia repair which overcomes the inherent disadvantages of known hernia repair methods and devices.

A hernia mesh support device formed in accordance with one form of the present invention has self-anchoring means allowing it to be securely attached to the peritoneum wall or pre-peritoneal tissue layers. The self-anchoring device minimizes the possibility of the intestines or omentum being trapped between the device and the peritoneum.

The hernia mesh support device, in one form of the present invention, includes a relatively stiff outer support ring having a first axial side and a second axial side situated opposite the first axial side. The outer ring supports a layer of mesh material and an anti-adhesion barrier on its second axial side. An inner ring is situated concentrically within the outer ring. A plurality of spaced apart spokes or ring support members extend radially between, and are attached to, a radially inner surface of the outer ring and a radially outer surface of the inner ring to join the two rings together. Thus, the spokes are sandwiched between the mesh material layer and the anti-adhesion barrier. The layer of mesh material and anti-adhesion barrier extend radially between and over the inner and outer rings with the mesh material being sandwiched between the anti-adhesion barrier on one side and the rings, and the spokes on the other side.

The inner ring includes a bore formed axially through at least a portion of the thickness thereof. A rib extends diametrically across the bore of the inner ring. A pull strap is loosely wrapped in half partially about the rib within the bore, and its two free ends may be pulled on by the surgeon to force the hernia mesh support device against the tissue, such as the peritoneum, to which the support device is to be affixed. Once the hernia mesh support device is affixed to the tissue, the pull strap may be removed from the hernia mesh support device by the surgeon releasing one free end and pulling on the other free end so the pull strap unwraps from around the inner ring rib. Alternatively, the pull strap may be used to further fixate the hernia mesh support in place by fixation with sutures or other fasteners.

The hernia mesh support device of the present invention preferably includes a plurality of barbed pins extending outwardly from a surface of the outer support ring on the first axial side thereof. The barbed pins are spaced apart from one another periodically about the circumference of the outer support ring. The barbed pins are provided to secure the hernia mesh support device to the peritoneum, pre-peritoneum tissue layers or other tissue.

The hernia mesh support device of the present invention further includes a removable protective cover. The removable protective cover is situated on the first axial side of the outer support ring and is disposed over the plurality of barbed pins extending therefrom, in order to protect the internal abdominal organs and tissue during deployment of the hernia mesh support device. One surface of the protective cover which faces the outer support ring may include an adhesive to retain the protective cover in place on the outer support ring, covering the barbed pins, until the protective cover is forcibly removed therefrom by the surgeon. The protective cover may include a pull string in the form of a loop, the ends of which are affixed to the protective cover. The surgeon would pull on the string loop at the appropriate time to remove the protective cover from the outer support ring in order to expose the barbed pins.

The hernia mesh support device fits tightly against the peritoneum while preventing intestinal or omental entrapment between the device and the peritoneum. After placement of the device inside the abdomen, the surgeon digitally sweeps the underlay of the device. After ensuring that no intestines or abdominal organs are present between the device and the body wall, the surgeon uncovers the barbed pins by pulling on the pull string attached to the cover that shields the barbed pins in a manner to prevent the barbed pins from causing injury to the abdominal organs. Immediately thereafter, the surgeon pulls on the device pull strap ends thereby placing the device tightly against the peritoneum and anchoring the barbed pins into the body wall.

In another embodiment of the present invention, the outer support ring of the hernia mesh support device carries a series of hollow needles, each of which is pre-loaded with a suture. After the needles penetrate the peritoneum and the fascia, the surgeon can pull and disengage these needles by inserting a tool, such as a needle holder or hemostats, and grabbing onto the pins. Locating the needles can be achieved by placing arrows or other indicia that point to or otherwise indicate the location of the hollow needles on the device. These arrows or other indicia are preferably placed on the inner ring of the device on the axial side thereof which is not covered by tissue and is, therefore, visible to the surgeon.

A preferred form of the hernia mesh support device as well as other embodiments, objects, features and advantages of this invention, will be apparent from the following detailed description of illustrative embodiments thereof, which is to be read in conjunction with the accompanying drawings.

DETAILED DESCRIPTION

The present invention is directed to an implantable surgical device and its method of use in the repair of hernial defects, trocar puncture wounds and the like.

Figure 1:
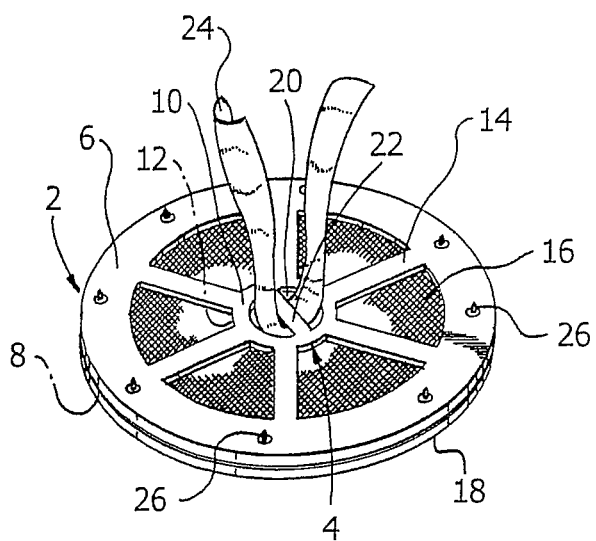
FIG. 1 is a perspective view of a first portion of an implantable hernia mesh support device formed in accordance with a first form of the present invention.
Figure 2:
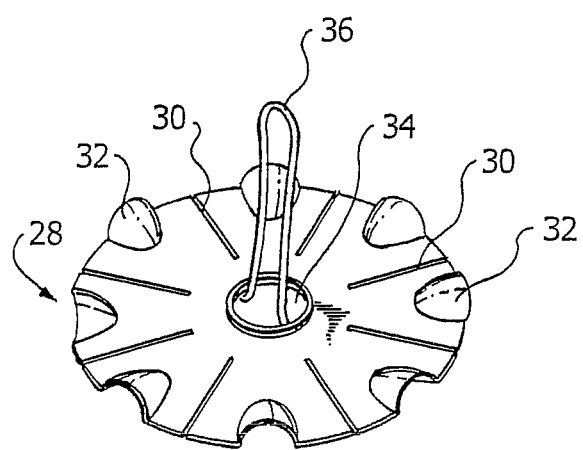
FIG. 2 is a perspective view of a second portion of the implantable hernia mesh support device formed in accordance with the first form of the present invention.
Figure 3:
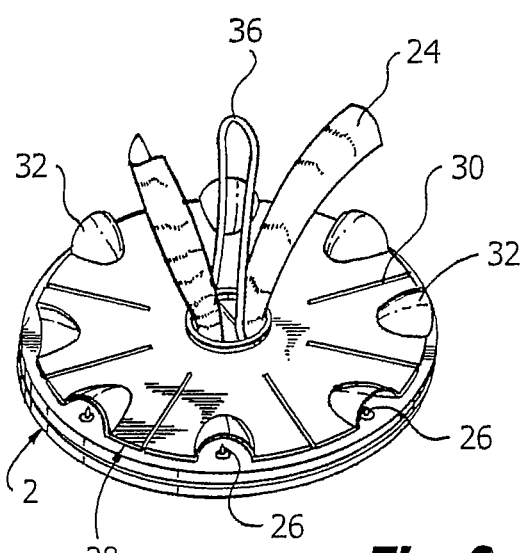
FIG. 3 is a perspective view of the implantable hernia mesh support device formed in accordance with the first form of the present invention and shown in an assembled form.

Referring initially to FIGS. 1-3 of the drawings, it will be seen that a hernia mesh support device constructed in accordance with a first form of the present invention includes a relatively stiff outer support ring 2 (which is stiffer than a mesh material used in the device), and an inner ring 4 (which may also be relatively stiff) which is situated concentrically radially within the outer support ring 2. The outer support ring 2 and the inner ring 4 reside in the same plane. The outer support ring 2 has a first axial side 6 and a second axial side 8 situated opposite the first axial side 6. Similarly, the inner ring 4 includes a first axial side 10 and a second axial side 12 situated opposite the first axial side 10, corresponding first axial sides 6, 10 and second axial sides 8, 12 of the outer support ring 2 and the inner ring 4 facing respectively in the same direction. The outer support ring 2 and inner ring 4 may be formed from a bioabsorbable or non-bioabsorbable material.

Spaced apart spokes or other ring support members 14 (which may also be made to be relatively stiff) extend radially between, and are attached to, a radially inner surface of the outer ring 2 and a radially outer surface of the inner ring 4 to join the two rings together. The spokes 14, like the outer support ring 2 and the inner ring 4, may be formed from a bioabsorbable material or a non-bioabsorbable material.

The hernia mesh support device further includes a layer of mesh material 16. The mesh material layer 16 is situated on the second axial sides 8, 12 of the outer support ring 2 and the inner ring 4 and extends at least between the two rings, from at least the radially inner surface of outer support ring 2 to at least the radially outer surface of the inner ring 4. The mesh material layer 16, as is well-known in the art, may be formed from a bioabsorbable or a non-bioabsorbable material, and defines a multiplicity of interstices through the thickness thereof to promote the ingrowth of tissue therethrough. Many different mesh materials are appropriate for use in the present invention and are well-known to those skilled in the art.

Figure 5:
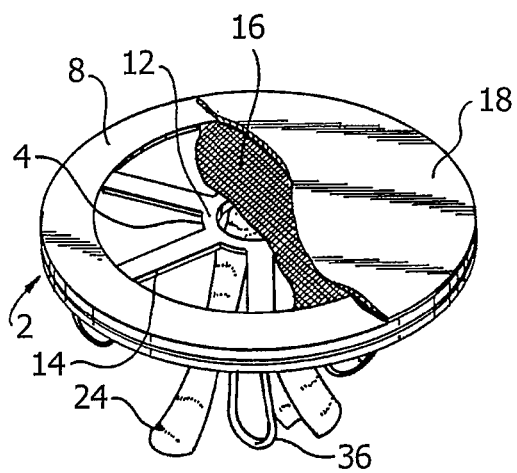
FIG. 5 is a perspective view of the underside of an implantable hernia mesh device of either the first or second form of the present invention, with portions thereof partially cut away.

As shown in FIG. 5, the hernia mesh support device of the present invention further includes an anti-adhesion barrier 18. The anti-adhesion barrier 18 is situated over the mesh material 16 on the second axial sides 8, 12 of the outer support ring 2 and the inner ring 4, and extends at least between the two rings, from at least the radially inner surface of the outer support ring 2 to at least the radially outer surface of the inner ring 4. The anti-adhesion barrier 18 may be formed from a material such as oxidized regenerated cellulose.

Accordingly, the hernia mesh support device of the present invention defines an axially laminated structure comprising the outer support ring 2 and the inner support ring 4, the layer of mesh material 16 and an anti-adhesion barrier 18 on one axial side of the rings.

As can be seen from FIG. 1 of the drawings, the inner ring 4 of the hernia mesh support device of the present invention includes a bore 20 formed axially through at least a portion of the thickness thereof. A rib 22 extends diametrically across the bore 20 of the inner ring 4. A pull strap 24 is loosely wrapped in half at its middle partially about the rib 22 within the bore 20, and has two free ends which thus extend out of the bore 20 on the first axial side 10 of the inner ring 4. This pull strap 24 may be pulled on by the surgeon to force the hernia mesh support device against the tissue, such as the peritoneum, to which the support device is to be affixed. Once the hernia mesh support device is affixed to the tissue, the pull strap 24 may be removed from the hernia mesh support device by the surgeon releasing one free end and pulling on the other free end so that the pull strap unwraps from around the inner ring rib 22. Alternatively, the pull strap may be used to further fixate the hernia mesh support in place by fixation with sutures or other fasteners. The hernia mesh support device of the present invention preferably includes a plurality of barbed pins 26 extending outwardly from a surface of the outer support ring 2 on the first axial side 6 thereof. The barbed pins 26 are spaced apart from one another periodically about the circumference of the outer support ring 2. The barbed pins 26 are provided to secure the hernia mesh support device to the peritoneum, pre-peritoneum tissue layers or other tissue in the patient's body.

As is shown in FIG. 2 of the drawings, the hernia mesh support device of the present invention further includes a removable protective cover 28. The protective cover 28 may be formed as a plastic film or sheet. The removable protective cover 28 is situated on the first axial side 6 of the outer support ring 2 and is disposed over the plurality of barbed pins 26 extending therefrom, as shown in FIG. 3 of the drawings, in order to protect the internal abdominal organs and tissue during deployment of the hernia mesh support device. One surface of the protective cover 28 which faces the outer support ring 2 may include an adhesive to releasably retain the protective cover in place on the outer support ring, covering the barbed pins 26, until the protective cover 28 is forcibly removed therefrom by the surgeon.

In the embodiment shown in FIG. 2 of the drawings, the preferred form of the protective cover 28 is generally cylindrical, and the protective cover includes a plurality of slits 30 extending radially inwardly from the outer peripheral edge of the cover. The protective cover 28 preferably includes a plurality of bulges or dimples 32 formed in the material of the cover near the peripheral edge of the cover, which bulges or dimples 32 are spaced apart from one another circumferentially about the protective cover 28 so that each bulge or dimple 32 may be positioned in alignment with and to cover a corresponding barbed pin 26 extending from the surface of the outer support ring 2. The radial slits 30 formed in the protective cover 28 provide the cover with greater flexibility to conform the shape of the outer support ring 2 and barbed pins 26 and to allow the portions of the protective cover between adjacent slits 30 on which the bulges or dimples 32 are formed to lift slightly out of the plane in which the protective cover resides when placed on the outer support ring 2 to ensure that the barbed pins 26 are fully covered and that the protective cover remains adhesively joined to the first axial side 6 of the outer support ring 2. Stated another way, the radial slits 30 that are evenly distributed about the circumference of the cover 28 enhance the overall flexibility of the cover to ensure that it may be adhesively joined to the outer ring 2 and at the same time cover the barbed pins 26 extending from the surface of the outer ring.

As can also be seen in FIG. 2 of the drawings, the protective cover 28 extends not only over the outer support ring 2 but also over the mesh material layer 16 situated between the outer support ring 2 and the inner support ring 4. Furthermore, the protective cover 28 includes a central opening 34 formed through the thickness thereof, which opening 34 can receive therethrough the ends of the pull strap 24 extending about the inner ring rib 22, as shown in FIG. 3 of the drawings. Additionally, the protective cover 28 may include a pull string 36 (also referred to as a cover release string) in the form of a loop, the ends of which are affixed to the protective cover 28 on diametrically opposite sides of that portion of the cover defining the central opening 34. The surgeon would pull on the cover release string 36 at the appropriate time to remove the protective cover 28 from the outer support ring 2 in order to expose the barbed pins 26.

The hernia mesh support device in its assembled form, as shown in FIG. 3, is inserted into the patient's abdomen after the hernia has been reduced in an open surgical approach. Subsequently, the surgeon digitally sweeps the space between the device and the abdominal wall, and clears away any abdominal contents that may be present there. Once the surgeon sweeps the space between the device and the abdominal wall, and confirms the non-entrapment of the abdominal organs, the cover release string 36 shown in FIG. 2 is pulled and the cover 28 is forcibly removed from the first axial side 6 of the outer support ring 2. This now exposes the barbed pins 26 to the peritoneum. The device is then pulled tighter against the abdominal wall by using the pull straps 24, thereby causing the barbed pins 26 to engage the abdominal wall tissue. The barbed pins 26 anchor the device closely to the peritoneum. This action also serves to position the device against the abdominal wall such that surrounding tissues and organs will no longer be exposed to the side of the device that adheres to the wall and, therefore, will neither come in contact with the mesh material layer 16 or the barbed pins 26 nor become entrapped between the device and the peritoneum.

Figure 4A:
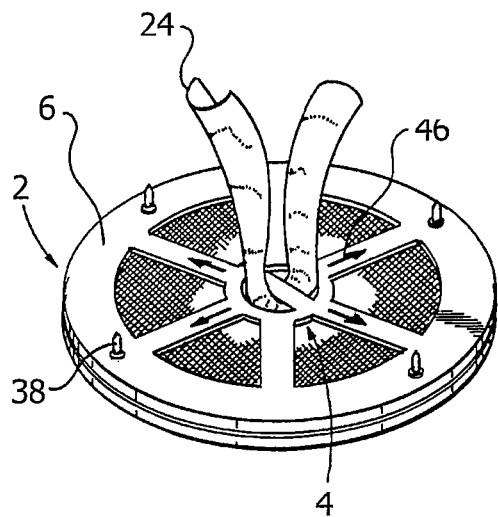
FIG. 4A is a perspective view of a first portion of an implantable hernia mesh support device formed in accordance with a second form of the present invention.
Figure 4B:
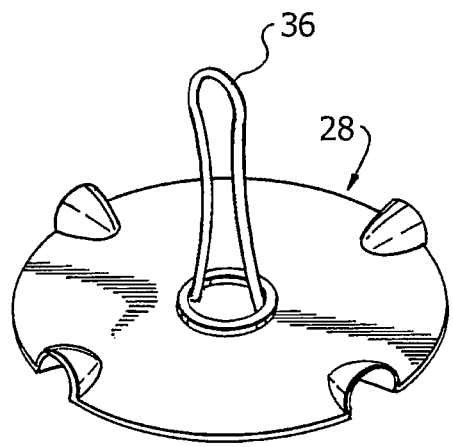
FIG. 4B is perspective view of a second portion of the implantable hernia mesh support device formed in accordance with the second form of the present invention.
Figure 4C:
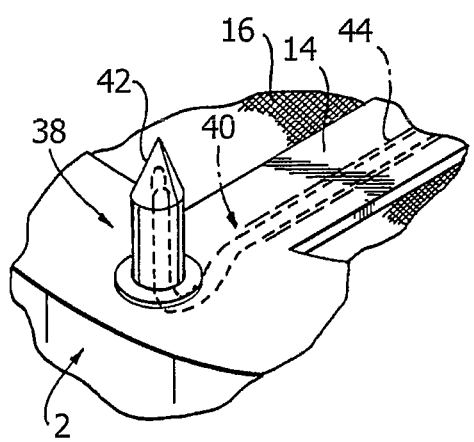
FIG. 4C is a partial perspective view of the implantable hernia mesh support device formed in accordance with the second form of the present invention, and further illustrating the details of a hollow needle loaded with a suture used in the second form of the present invention.

FIGS. 4A-4C illustrate a second embodiment of a hernia mesh support device constructed in accordance with the present invention. This second embodiment has the same structure as the first embodiment described previously and shown in FIGS. 1-3, except that the barbed pins 26 of the first embodiment are now replaced with hollow detachable needles 38 that are pre-loaded with sutures 40. More specifically, each suture 40 is preferably in the form of an elongated loop, with one end of the loop passing through the bore of the hollow needle 38 and attached to the tip 42 situated at the free end thereof, and with the other end of the loop being attached to either the outer ring 2, the inner ring 4, or an interconnecting spoke 14. The hollow needles 38 are mounted to and extend outwardly from the first axial side 6 of the outer support ring 2, which may include one or more passageways 44 for receiving the suture 40, which passageways 44 communicate with the bores of the hollow needles 38. The hollow needles 38 are attached to the outer support ring 2 in such a manner that would allow them to disengage from the outer support ring by the surgeon using a tool, such as a needle holder or hemostats, and grabbing onto the hollow needles 38. Thus, by using hollow needles 38 pre-loaded with sutures 40, the sutures can be driven through the peritoneum and other layers of the body wall such as fascial layers and muscular layers. Each suture 40, which is hidden in the needle 38 and secured to the structure of the hernia mesh support device, is released. Hence, the needle 38 serves as a "harpoon" to drive the suture 40 through one or more layers of the body wall.

The second embodiment of the hernia mesh support device of the present invention illustrated by FIGS. 4A-4C is implanted in a manner that is similar to that used with the first embodiment shown in FIGS. 1-3. After the hollow needles 38 penetrate one or more layers of the body wall, the surgeon can pull and disengage these needles from outer support ring using needle holders or hemostats, that are pushed bluntly through the muscular layer and below the skin, and grabbing onto the hollow needles. Locating the hollow needles 38 may be achieved by placing arrows 46 or other indicia in the middle of the device, such as on the inner ring 4 or the spokes 14, where the device is not covered by tissue and is visible to the surgeon in an open or minimally invasive procedure. The arrows 46 or other indicia are preferably situated on the first axial side 10 of the inner ring 4 that faces the surgeon after the device is deployed. The arrows 46 or other indicia point to the location of the hollow needles 38.

The surgeon pulls on the sutures 40 to the middle of the device, where the device is exposed, and then the sutures can be tied to each other, thereby pulling the outer support ring 2 of the device towards the peritoneum.

The hernia mesh support device of the present invention allows better incorporation of the hernia device to the peritoneum, thereby increasing the degree of tissue integration with the device. This, in turn, increases the strength of the repair of the hernia. Also, the hernia mesh support device of the present invention minimizes or eliminates the possibility of intestinal entrapment between the device and the peritoneum. Such entrapment could have otherwise resulted in obstruction and strangulation of the entrapped tissue as well as the formation of adhesions between the peritoneum, bowel, and other abdominal organs. Avoidance of adhesions are especially important for women who may later become pregnant. For these patients, it is crucial that the abdominal contents will be able to move. The tearing of adhesions following pregnancy due to entrapment can be very painful and may require additional surgery. Such is avoided with the present invention. Also, the hollow needles that can detach from the hernia mesh support device of the present invention and which carry sutures with them prevent the need to use the blind approach for anchoring the mesh to the peritoneum or pre-peritoneal layers. The protective cover of the hernia mesh support device of the present invention protects the barbed pins or hollow needles from injuring the abdominal organs, and may be easily removed during deployment of the device.

Although illustrative embodiments of the present invention have been described herein with reference to the accompanying drawing, it is to be understood that the invention is not limited to those precise embodiments, and that various other changes and modifications may be effected therein by one skilled in the art without departing from the scope or spirit of the invention.

What is claimed is:

1. A method of repairing a hernia using a hernia mesh support device comprising:

providing a hernia mesh support device which comprises an outer ring, an inner ring situated concentrically within the outer ring and being co-planarly arranged therewith, each of the outer ring and the inner ring having a first axial side and a second axial side situated opposite the first axial side, a plurality of spaced apart ring support members extending between and interconnected to the outer ring and the inner ring, a layer of mesh material, the layer of mesh material being situated at the first axial side of the outer and inner rings and at least extending between the outer and inner rings, an anti-adhesion barrier, the anti-adhesion barrier being situated at the second axial side of the outer and inner rings and at least extending between the outer and inner rings, a plurality of barbed pins, each of the barbed pins being mounted on the outer ring and extending outwardly from the first axial side thereof, the barbed pins being spaced apart from one another about the circumference of the outer ring, a removable protective cover, the protective cover being situated on the first axial side of the outer ring and disposed over the plurality of barbed pins extending therefrom, and a pull strap, the pull strap being joined to the inner ring and extending outwardly from the first axial side thereof;

reducing a hernia within a patient's abdomen;

inserting the hernia mesh support device into the abdomen and positioning the device in alignment with the hernia;

ensuring that no abdominal organs are present between the device and an abdominal wall, wherein the ensuring that no abdominal organs are between the device and the abdominal wall includes a step of digitally sweeping a space between the abdominal wall and the device;

removing the protective cover; and pulling on the pull strap joined to the inner ring to place the device tightly against the abdominal wall and to anchor the barbed pins into the abdominal wall, wherein the inner ring has formed therein a bore extending at least partially through a thickness thereof, wherein the hernia mesh support device further comprises a rib extending diametrically across the bore of the inner ring, and wherein the pull strap is removably mounted to the rib.

2. The method as claimed in claim 1, wherein the pull strap includes two free ends which extend outwardly from the first axial side of the inner ring, the strap including a middle portion, the middle portion being partially wrapped about the rib of the inner ring.

3. The method as claimed in claim 2, wherein the removable protective cover is formed of a sheet-like material and includes an outer peripheral edge and a central opening formed through a thickness thereof, the protective cover being situated on the first axial side of the outer ring and the first axial side of the inner ring and extending over the outer ring and the inner ring, the central opening formed in the protective cover being situated in alignment with the inner ring to receive therethrough the pull strap joined to the inner ring.

4. The method as claimed in claim 3, wherein the protective cover includes a cover release string mounted thereon and extending therefrom.

5. The method as claimed in claim 3, wherein the protective cover includes a plurality of slits formed through the thickness thereof and extending radially inwardly from the outer peripheral edge of the protective cover.

6. The method as claimed in claim 3, wherein the protective cover includes a plurality of dimples, each dimple of the plurality of dimples being situated near the outer peripheral edge of the protective cover and in alignment with and to cover a corresponding one of the barbed pins.

7. The method as claimed in claim 1, wherein the anti-adhesion barrier is formed from an oxidized regenerated cellulose.

8. The method as claimed in claim 1, wherein at least one of the inner ring, the outer ring and the plurality of spaced apart ring support members is formed of a bioabsorbable material.

9. The method as claimed in claim 1, wherein at least one of the inner ring, the outer ring and the plurality of spaced apart ring support members is formed of a non-bioabsorbable material.

10. The method as claimed in claim 1, wherein at least one of the outer ring, the inner ring and the plurality of spaced apart ring support members is stiffer than the layer of mesh material.

11. The method as claimed in claim 1, further comprising a plurality of markings situated on the first axial side of the inner ring, the markings being disposed to point to the barbed pins.

12. A method of repairing a hernia using a hernia mesh support device comprising:

providing a hernia mesh support device which comprises an outer ring, an inner ring situated concentrically within the outer ring and being co-planarly arranged therewith, each of the outer ring and the inner ring having a first axial side and a second axial side situated opposite the first axial side, a plurality of spaced apart ring support members extending between and interconnected to the outer ring and the inner ring, a layer of mesh material having interstices through a thickness thereof to promote tissue ingrowth, the layer of mesh material being situated at the first axial side of the outer and inner rings and at least extending between the outer and inner rings, an anti-adhesion barrier, the anti-adhesion barrier being situated at the second axial side of the outer and inner rings and at least extending between the outer and inner rings, a plurality of barbed pins, each of the barbed pins being mounted on the outer ring and extending outwardly from the first axial side thereof, the barbed pins being spaced apart from one another about the circumference of the outer ring, a removable protective cover, the protective cover being situated on the first axial side of the outer ring and disposed over the plurality of barbed pins extending therefrom, and a pull strap, the pull strap being joined to the inner ring and extending outwardly from the first axial side thereof;

reducing a hernia within a patient's abdomen;

inserting the hernia mesh support device into the abdomen and positioning the device in alignment with the hernia;

ensuring that no abdominal organs are present between the device and an abdominal wall, wherein the ensuring that no abdominal organs are between the device and the abdominal wall includes a step of digitally sweeping a space between the abdominal wall and the device;

removing the protective cover; and pulling on the pull strap joined to the inner ring to place the device tightly against the abdominal wall and to anchor the barbed pins into the abdominal wall, wherein the removable protective cover is formed of a sheet-like material and includes an outer peripheral edge and a central opening formed through a thickness thereof, the protective cover being situated on the first axial side of the outer ring and the first axial side of the inner ring and extending over the outer ring and the inner ring, the central opening formed in the protective cover being situated in alignment with the inner ring to receive therethrough the pull strap joined to the inner ring.

13. The method as claimed in claim 12, wherein the inner ring has formed therein a bore extending at least partially through a thickness thereof, wherein the hernia mesh support device further comprises a rib extending diametrically across the bore of the inner ring, and wherein the pull strap is removably mounted to the rib.

14. The method as claimed in claim 13, wherein the pull strap includes two free ends which extend outwardly from the first axial side of the inner ring, the strap including a middle portion, the middle portion being partially wrapped about the rib of the inner ring.

15. The method as claimed in claim 12, wherein the protective cover includes a cover release string mounted thereon and extending therefrom.

16. The method as claimed in claim 12, wherein the protective cover includes a plurality of slits formed through the thickness thereof and extending radially inwardly from the outer peripheral edge of the protective cover.

17. The method as claimed in claim 12, wherein the protective cover includes a plurality of dimples, each dimple of the plurality of dimples being situated near the outer peripheral edge of the protective cover and in alignment with and to cover a corresponding one of the barbed pins.

18. A method of repairing a hernia using a hernia mesh support device comprising:
  providing a hernia mesh support device which comprises
    an outer ring,
    an inner ring situated concentrically within the outer ring and being co-planarly arranged therewith, each of the outer ring and the inner ring having a first axial side and a second axial side situated opposite the first axial side,
    a plurality of spaced apart ring support members extending between and interconnected to the outer ring and the inner ring,
    a layer of mesh material having interstices through a thickness thereof to promote tissue ingrowth, the layer of mesh material being situated at the first axial side of the outer and inner rings and at least extending between the outer and inner rings,
    an anti-adhesion barrier, the anti-adhesion barrier being situated at the second axial side of the outer and inner rings and at least extending between the outer and inner rings,
    a plurality of barbed pins, each of the barbed pins being mounted on the outer ring and extending outwardly from the first axial side thereof, the barbed pins being spaced apart from one another about the circumference of the outer ring,
    a removable protective cover, the protective cover being situated on the first axial side of the outer ring and disposed over the plurality of barbed pins extending therefrom, and
    a pull strap, the pull strap being joined to the inner ring and extending outwardly from the first axial side thereof;
  reducing a hernia within a patient's abdomen;
  inserting the hernia mesh support device into the abdomen and positioning the device in alignment with the hernia;
  ensuring that no abdominal organs are present between the device and an abdominal wall, wherein the ensuring that no abdominal organs are between the device and the abdominal wall includes a step of digitally sweeping a space between the abdominal wall and the device;
  removing the protective cover; and
  pulling on the pull strap joined to the inner ring to place the device tightly against the abdominal wall and to anchor the barbed pins into the abdominal wall, wherein the protective cover includes a plurality of slits formed through a thickness thereof and extending radially inwardly from an outer peripheral edge of the protective cover.

19. The method as claimed in claim 18, wherein the inner ring has formed therein a bore extending at least partially through a thickness thereof, wherein the hernia mesh support device further comprises a rib extending diametrically across the bore of the inner ring, and wherein the pull strap is removably mounted to the rib.

20. The method as claimed in claim 18, wherein the pull strap includes two free ends which extend outwardly from the first axial side of the inner ring, the strap including a middle portion, the middle portion being partially wrapped about the rib of the inner ring.

* * * * *